(12) United States Patent
Gutman et al.

(10) Patent No.: US 6,552,155 B1
(45) Date of Patent: Apr. 22, 2003

(54) POLYALDIMINES OF OLIGOMERIC AMINOBENZOIC ACID DERIVATIVES, AND THEIR USE FOR PREPARATION OF MOISTURE-CURABLE, STORAGE-STABLE, ONE-PART POLYREAS

(75) Inventors: Arie Gutman, Haifa (IL); Gennadiy Nisnovich, Haifa (IL); Igor Zaltzman, Haifa (IL); Lev Judovich, Haifa (IL); Vladimir Kuznetsov, Nesher (IL)

(73) Assignee: Kenneth I. Sawyer, Nanuet, NY (US)

( * ) Notice: Subject to any disclaimer, the term of this patent is extended or adjusted under 35 U.S.C. 154(b) by 0 days.

(21) Appl. No.: 09/959,430

(22) PCT Filed: Apr. 23, 2000

(86) PCT No.: PCT/IL00/00237

§ 371 (c)(1),
(2), (4) Date: Oct. 25, 2001

(87) PCT Pub. No.: WO00/64860

PCT Pub. Date: Nov. 2, 2000

(30) Foreign Application Priority Data

Apr. 25, 1999 (IL) .................................. 129583

(51) Int. Cl.[7] ........................ C08G 18/32; C08G 18/30; C08G 18/50; C08G 18/38; C07C 251/02
(52) U.S. Cl. ................. 528/68; 427/385.5; 427/388.1; 428/423.1; 428/425.8; 528/62; 528/63; 528/64; 528/84; 560/19; 560/50; 564/271; 564/272; 564/274; 564/275
(58) Field of Search ............................ 528/62, 63, 64, 528/68, 84; 560/19, 50; 564/271, 272, 274, 275; 427/385.5, 388.1; 428/423.1, 425.8

(56) References Cited

U.S. PATENT DOCUMENTS

| 3,817,940 A | 6/1974 | Blahak et al. ............. 528/68 |
| 3,929,863 A | 12/1975 | Blahak et al. ............. 560/50 |
| 3,932,360 A | 1/1976 | Cerankowski et al. ........ 528/64 |
| 4,007,239 A | 2/1977 | Blahak et al. ............. 558/251 |
| 4,328,322 A | 5/1982 | Baron ..................... 521/163 |
| 4,720,535 A | 1/1988 | Schleier et al. ........... 528/59 |
| 5,162,481 A | 11/1992 | Reid et al. ............... 528/48 |
| 6,297,320 B1 * | 10/2001 | Tang et al. ............... 525/107 |

FOREIGN PATENT DOCUMENTS

GB     1064841    4/1967

OTHER PUBLICATIONS

Lin, Q., et al., "Synthesis and characterization of new Schiff–base coordination polymers," *Chem. Abstracts* 129:1084, Abs. No. 350165r, American Chemical Society (Dec. 1998).

Mark, H.F., et al., "Polyureas," in: *Encyclopedia of Polymer Science and Engineering*. vol. 13, *Poly(phenylene Ether) to Radical Polymerization*, Mark, H.F., et al., eds., John Wiley & Sons, Inc., New York, New York, pp. 212–217 (1988).

Smith, M.B. and March, J., "Hydrolysis of the Carbon–Nitrogen Double Bond," in: *March's Advanced Organic Chemistry, Reactions, Mechanisms, and Structure. Fifth Edition.*, Smith, M.B. and March, J., eds., John Wiley & Sons, Inc., New York, New York, p. 1177 (Jan. 2001).

* cited by examiner

*Primary Examiner*—Rabon Sergent
(74) *Attorney, Agent, or Firm*—Sterne, Kessler, Goldstein & Fox P.L.L.C.

(57) ABSTRACT

The invention relates to polyaldimines of formula [1] and their use within moisture curable one part polyurea compositions.

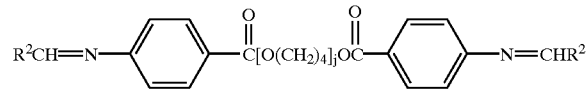

[1]

wherein j is an integer of 3 to 30 and $R^2$ is unsubstituted homocyclic or heterocyclic aryl radical or alkyl, alkoxy, alkylthio or halogen substituted homocyclic or heterocyclic aryl radical.

23 Claims, 1 Drawing Sheet

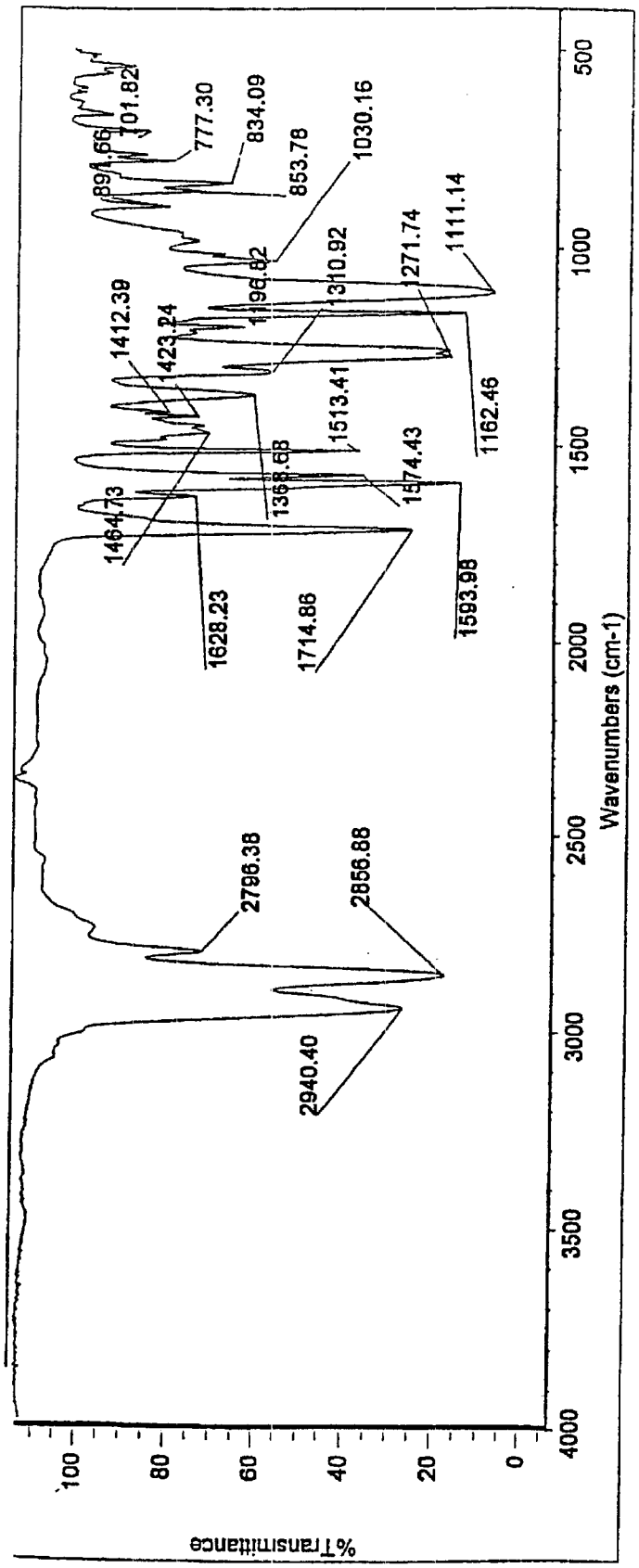

POLYALDIMINES OF OLIGOMERIC AMINOBENZOIC ACID DERIVATIVES, AND THEIR USE FOR PREPARATION OF MOISTURE-CURABLE, STORAGE-STABLE, ONE-PART POLYREAS

This Application is a U.S. National Phase Application of International Application No. PCT/IL00/00237, filed on Apr. 23, 2000, which was published under PCT Article 21(2) in English and claims priority to Israel Patent Application No. 129583 filed Apr. 25, 1999, both of which are incorporated herein by reference.

FIELD OF THE INVENTION

The present invention relates to using of new polyaldimines with aromatic polyisocyanates for preparing moisture curable and storage stable compositions.

BACKGROUND OF THE INVENTION

Mixing of poly(1,4-butanediol)bis(4-aminobenzoate) with polyisocyanate gives polymers, which exhibit excellent physicochemical properties (U.S. Pat. No. 4,328,322). In these two component compositions curing speed can be controlled, but the following operations are required: to measure each component exactly on the site, to mix the two components until a uniform mixture is obtained shortly before application thereof and to use the mixture within the pot life, which is usually not longer than one hour. Therefore, a disadvantage of this process is that often under difficult conditions on construction sites one must work with complicated and expensive mixing units having to perform all operations quickly and without the possibility to store the mixture for any length of time.

Thus, it is strongly desired to develop a storage stable one component polymer composition which consists of N-protected poly(1,4-butanediol)bis(4-aminobenzoate) and organic polyisocyanate and may be rapidly cured by atmospheric moisture after application to give polymers, with physicochemical properties similar to those of polymers prepared by mixing poly(1,4-butanediol)bis(4-aminobenzoate) with organic polyisocyanates.

SUMMARY OF THE INVENTION

It is an object of the present invention to provide a novel process for the preparation of polyurea polymers, which does not require measuring and mixing components at the time and on the site of application. The properties of the polymers obtained by this novel process should be equivalent to those of the polymers prepared by mixing of a polyisocyanate with an poly(1,4-butanediol)bis(4-aminobenzoate).

It is a further object of this invention to provide novel compositions and intermediates for the above process.

The above objects are achieved by the present invention, which provides by a first of its aspects new moisture tempered, storage stable single component polyurea compositions, comprising of:

(i) a compound or mixture of compounds of formula [1]:

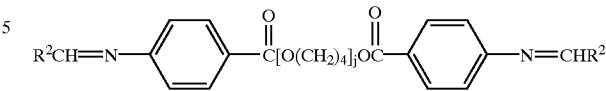

[1]

wherein j is an integer of 3 to 30 and $R^2$ is unsubstituted aryl or heterocyclic aryl radical or alkyl, alkoxy, alkylthio or halogen substituted aryl or heterocyclic aryl radical;

(ii) an aromatic polyisocyanate and/or a polyurethane/urea prepolymer having terminal aromatic isocyanate groups; and (iii) a protic acid or salts thereof.

According to another aspect the present invention provides a new process for preparing a synthetic polymer, comprising:

(i) reacting a poly(1,4-butanediol)bis(4-aminobenzoate) [2]:

[2]

wherein j is an integer of 3 to 30;
with a substantially equivalent amount of an aromatic aldehyde represented by the formula [3]:

$R^2CH=O$            [3]

wherein $R^2$ is unsubstituted aryl or heterocyclic aryl radical or alkyl, alkoxy, alkylthio or halogen substituted aryl or heterocyclic aryl radical;
to give a polyaldimine, represented by the formula [1]:

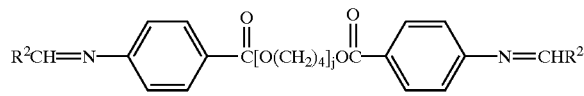

[1]

wherein j and $R^2$ are the same as above;

(ii) mixing the polyaldimine [1] with an aromatic polyisocyanate and a catalytic quantity of a protic acid or salts thereof, and optionally adding to the mixture auxiliary agents and/or additives;

(iii) exposing the obtained mixture to water or air humidity at the time of application on site to cause curing.

The new polyaldimines [1], that are obtained as intermediates in the first stage of the process of the present invention, represent a further aspect of the invention.

BRIEF DESCRIPTION OF THE DRAWING

FIG. 1—IR spectrum of compound [1a].

DETAILED DESCRIPTION OF THE INVENTION

The present invention provides novel blocked polyamine [1], which is stable either per se or in a mixture with organic polyisocyanates and upon hydrolysis easily generates poly(1,4-butanediol)bis(4-aminobenzoate).

The present invention also provides a process for the preparation of compound [1] which comprises reacting a poly(1,4-butanediol)bis(4-aminobenzoate) [2] with an aromatic aldehyde [3] according to Scheme 1:

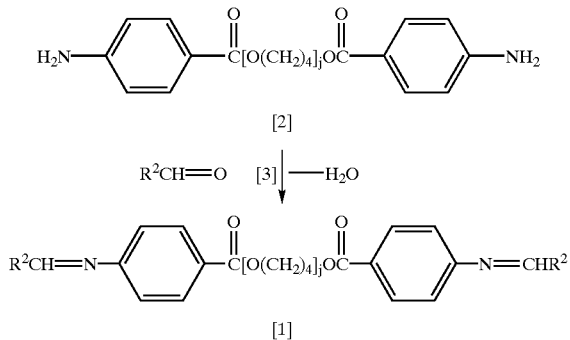

wherein j and $R^2$ are the same as above.

Preferably, the aldehyde is selected from the group consisting of benzaldehyde, anisaldehyde, furfural, ethoxybenzaldehyde, butoxybenzaldehyde, hexyloxybenzaldehyde, octyloxybenzaldehyde, decyloxybenzaldehyde, dodecyloxybenzaldehyde, hexadecyloxybenzaldehyde, ethylbenzaldehyde, isopropylbenzaldehyde, dimethylbenzaldehyde, furfural and pyridinecarboxaldehyde.

Polyaldimines [1] of the present invention may be prepared by the following procedure:

Poly(1,4-butanediol)bis(4-aminobenzoate) [2] is heated with two or more moles of aldehyde [3] to allow dehydration reaction. The water generated in the reaction is distilled out azeotropically or absorbed by molecular sieves or reacted with a water sponge. These reactions may be carried out with or without solvents After completion of the reaction the solvent is distilled from the reaction mixture to obtain the desired aldimine [1].

The water sponge may be organic mono- or polyisocyanate. Preferably, the solvent is toluene, xylene, cyclohexane or heptane.

A moisture curable, storage stable, single component polyurea composition of the present invention may be prepared by mixing the following components under reduced pressure or in an inert atmosphere:

(i) a compound or mixture of compounds of formula [1];
(ii) aromatic polyisocyanates and/or polyurethane/urea prepolymer having terminal aromatic isocyanate groups; and
(iii) a protic acid or salt thereof.

Preferably the aromatic polyisocyanate is an aromatic diisocyanate, a carbodiimide modified polyisocyanate, biuret modified polyisocyanate, isocyanurate modified polyisocyanate or urethone modified polyisocyanate. Preferably the said aromatic diisocyanates are toluene diisocyanates or diphenylmethane diisocyanates including various mixtures of isomers thereof.

The polyurethane prepolymer having terminal aromatic isocyanate groups can be prepared by reacting an excess of aromatic polyisocyanate with polyol or polyamine, so that two or more free isocyanate groups remain in the resulting prepolymer.

The ratio of the number of amino groups in the polyamine formed by the hydrolysis of polyaldimine to the number of isocyanate groups contained in the polyisocyanate and/or the polyurethane/urea prepolymer having terminal aromatic isocyanate groups is from 0.5 to 2.0, preferably from 0.7 to 1.5.

Preferably, the protic acids are selected from the group consisting of carboxylic, sulfonic or phosphoric acids. Examples of carboxylic acids are aromatic carboxylic acids, while examples of sulfonic acids are aromatic or aliphatic sulfonic acids. The amount of the protic acids is preferably in the range of from 0.05 to 5% by weight of the composition.

Storage stability of the composition in a hermetically sealed package may exceed 6 months at room temperature.

Moisture curable marine anti-fouling paints and anticorrosive coatings were developed based on the polyurea compositions of the invention. The paints and coatings protect metal and non-metal surfaces from corrosive action of acid and salt water and inhibit the fixation of marine organisms on structures, which are immersed in seawater. Coats of the paints to be applied to the ship's hull can at least preserve the ship's service efficiency during the life of the top coat paint and may in some circumstances lead to an improvement in that efficiency during service.

Moisture curable polyurea compositions of this invention are used, for example, for wall and roof covering material, waterproof, or flooring materials, caulking, sealing, paint, coating and adhesive. In order to control viscosity, resin properties, and service life depending upon the uses, auxiliary agents and/or additives can be incorporated into the moisture curable polyurea composition of the invention.

Preferably, the auxiliary agents and/or additives are fillers, thixotropic agents, plasticizers, adhesion improvers, metallic powders, inorganic or organic colorants, stabilizers, biocides and solvents.

Useful fillers include, for example, calcium carbonate, talc, kaolin, aluminum sulfate, zeolite, diatomaceous earth, polyvinylchloride paste resin, glass balloon and polyvinylidene chloride resin balloon.

Exemplary thixotropic agents, which can be used, include colloidal silica, fatty acid amide wax, aluminum stearate, surface treated bentonite, polyethylene short fiber, and phenol resin short fiber.

Useful plasticizers include, for example, dioctyl phthalate, dibutyl phthalate, dilauryl phthalate, butyl benzyl phthalate, dioctyl adipate, diisodecyl adipate, diisodecyl phthalate and trioctyl phosphate.

Exemplary adhesion improvers which can be preferably used in the invention include known silane coupling agents.

Examples of the metallic powder include metal flakes such as aluminum flakes, nickel flakes, stainless steel flakes, titanium flakes and bronze flakes. One type of metallic powder can be used individually, or a combination of two or more types can be used. The metallic powder can be blended in the range of preferably from 0.1 to 20% by weight of the composition.

Examples of the inorganic colorants include carbon black, graphite, molybdenum disulfide, titanium oxide, chromium oxide, iron oxide based colored pigments such as iron oxide red; and complex metal oxide based colored pigments such as composite inorganic oxide yellow and baked pigment.

Examples of the organic colorants include phthalocyanine based colored pigments such as phthalocyanine green and phthalocyanine blue; perylene based colored pigments such as perylene red and perylene maroon; indanthrone based colored pigments such as indanthrone blue; azomethine based colored pigments such as azomethine yellow; benzimidazolone based colored pigments such as benzimidazolone yellow and benzimidazolone orange; quinacridone based colored pigments such as quinacridone orange, red, violet and quinacridone magenta; anthraquinone based colored pigments such as anthraquinone yellow, red; diketopyrrolopyrrole based colored pigments such as diketopyrrolopyrrole orange, red; isoindolinone based colored pigments such as isoindolinone yellow and orange, phthalimide based colored pigments such as phthalimide yellow and dioxazine based colored pigments such as dioxazine violet.

The colorants can be blended in the range of preferably from 0.1 to 5% by weight of the composition. One type of colorant can be used individually, or a combination of two or more types can be used Sterically hindered phenol compounds, triazol compounds and other stabilizers can be added in the range of from 0.1 to 2% by weight of the composition.

When the additives have high moisture content, these additives must previously be dehydrated.

The moisture curable polyurea composition thus obtained can be used either immediately, or can be stored in a sealed container under an inert atmosphere. Under such conditions, the composition has very good storage stability, high retention of physical properties and good stability of viscosity even if stored at increased temperatures. On the other hand, when the seal is broken, the atmospheric moisture cures the composition. It should be noted that in parallel with the desired reaction of aldimine hydrolysis, a side reaction may take place, i.e. hydrolysis of isocyanate groups with the evolution of carbon dioxide. The amino groups so formed further react with available isocyanate groups to form urea linkages. Solid polyurea products having excellent physico-chemnical properties can thus be obtained, which property is quite different from conventional, moisture curable polyurethane.

The moisture curable polyurethane/urea compositions of the invention are excellent in curing ability and in storage stability for long periods. The compositions provide sealing materials, wall covering materials, and waterproof materials, flooring materials, paints and adhesives depending upon the object for use. These materials have also excellent storage stability and workability, and can be cured rapidly by atmospheric moisture on application in site. Further, the cured products have high hydrolytic stability and modulus and excellent strength.

The invention will now be described in greater detail in the following non-limiting examples with reference to the accompanying drawing in which:

FIG. 1—IR spectrum of compound [1a].

EXAMPLE 1

Poly(1,4-butanediol)bis[4-[(4-anisylmethylene) amino]benzoate] [1a]

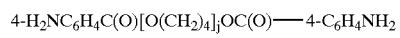

[2a]

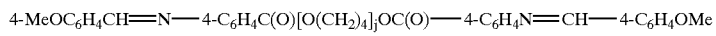

[1a]

Scheme 2

A 500 mL glass reactor equipped with a heating mantle, a magnetic stirrer, a Dean-Stark trap with condenser and bubbler was charged with poly(1,4-butanediol)bis(4-aminobenzoate) [2a] (Versalink™ P-1000, Air Products Corp.) (50.0 g), p-anisaldehyde [3a] (14.3 g), benzoic acid (0.5 g) and toluene (200 mL) under nitrogen. The mixture was refluxed for 5 hours during which time the water was formed. The reaction mixture was evaporated at 85° C. under reduced pressure (1-2 mbar) to a constant weight to give the desired poly(1,4-butanediol)bis[4-[(4-anisylmethylene)amino]benzoate][1a] as a yellowish liquid. The IR spectrum of the reaction product has a characteristic absorption of —N=C— at 1715 cm$^{-1}$ as illustrated in FIG. 1.

EXAMPLES 2–10

Poly(1,4-butanediol)bis[4-[(R$^2$-methylene)amino] benzoate] [1b-k]

General Procedure

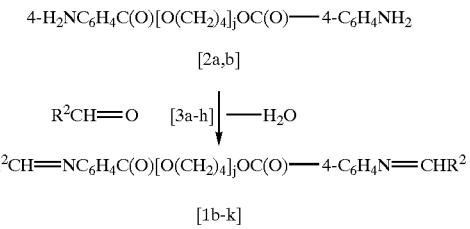

Scheme 3

Poly(1,4-butanediol)bis(4-aminobenzoate) Versalink™ P-1000 [2a] or P-650 [5b] (1.0 mol, both from Air Products Corp.) and aldehyde [3a-h] (2.0–2.5 mol) were condensed in an inert solvent (toluene, heptane or cyclohexane) in the presence of benzoic or p-toluenesulfonic acid (0.5–2 wt. %) until the expected amount of water had separated in a water collecting device. Following this, the mixture was evaporated under vacuum IR spectrum confirmed the formation of —N=C— bonds in the residue.

The initial materials used and the resulting aldimines are summarized in Table 1.

TABLE 1

| Preparation of aldimines [1b-k] | | | |
|---|---|---|---|
| Example | Polyamine | Aldehyde | Aldimine |
| 2 | [2a] | 4-Tolualdehyde [3b] | [1b] |
| 3 | [2a] | 4-Isopropylbenzaldehyde [3c] | [1c] |
| 4 | [2a] | 2,5-Dimethylbenzaldehyde [3d] | [1d] |
| 5 | [2a] | 4-Dodecyloxybenzaldehyde [3e] | [1e] |
| 6 | [2a] | Veratraldehyde [3f] | [1f] |

TABLE 1-continued

Preparation of aldimines [1b-k]

| Example | Polyamine | Aldehyde | Aldimine |
|---------|-----------|----------|----------|
| 7 | [2a] | Furfural [3g] | [1g] |
| 8 | [2a] | 4-Pyridinecarboxaldehyde [3h] | [1h] |
| 9 | [2b] | 4-Tolualdehyde [3b] | [1j] |
| 10 | [2b] | 4-Anisaldehyde [3a] | [1k] |

EXAMPLE 11

Preparation of the Moisture Curable Polyrea Composition

General Procedure

An aldimine, prepared according to Examples 1–10, or a mixture of aldimines was mixed together with such a quantity of carbodiimide modified diphenylmethane diisocyanate Isonate™ 2143L (obtained from Dow Chemical Company), so that the ratio of —NCO groups to aldimino groups was 1.0–1.5. The mixture was stirred under reduced pressure for 0.5 h at 50° C.

The obtained mixture was applied to a glass plate to give a layer 0.5–1 mm thick and allowed to stand at 25° C. under relative humidity of 60% for 24 hours and after this time the coated films showed ≧IH pencil hardness without any significant disturbing of polymer homogeneity. When Isonate™ 2143L alone was treated by the same procedures as above, no surface curing was observed after 24 hours.

After storage for 14 days at 50° C. under sealed conditions, it was found that the properties of the compositions did not show any significant changes.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Compounds of formula [1]

[1]

wherein j is an integer of 3 to 30 and $R^2$ is unsubstituted homocyclic or heterocyclic aryl radical or alkyl, alkoxy, alkylthio or halogen substituted homocyclic or heterocyclic aryl radical.

2. Compound [1] according to claim 1 wherein $R^2$ is selected from the group consisting of phenyl, methoxyphenyl, ethoxyphenyl, butoxyphenyl, hexyloxybenyl, octyloxyphenyl, decyloxyphenyl, dodecyloxyphenyl, hexadecytoxyphenyl, ethylphenyl, isopropylphenyl, dimethylphenyl, furyl and pyridyl.

3. Compound [1] according to claim 1 or 2 wherein j is an integer of 13 to 14.

4. A method for preparing a moisture curable, storage stable, one part composition, comprising mixing:
   (i) a compound of claim 1;
   (ii) an aromatic polyisocyanate, a polyurethane/urea prepolymer having terminal aromatic isocyanate groups, or mixtures thereof;
   (iii) a protic acid or salts thereof; and optionally
   (iv) one or more auxiliary agents, additives, or mixtures thereof.

5. The method of claim 4, wherein the composition is prepared under reduced pressure or in an inert atmosphere.

6. The method of claim 4, wherein the polyurethane prepolymer is prepared by reacting an excess of aromatic polyisocyanate with polyol or polyamine.

7. The method of claim 4, wherein the auxiliary agents and/or additives are selected from the group consisting of fillers, thixotropic agents, plasticizers, adhesion improvers, metallic powders, inorganic or organic colorants, stabilizers, biocides, and solvents.

8. A method for the preparation of compounds of formula [1]:

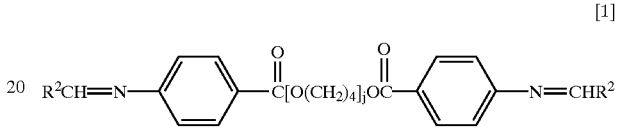

[1]

comprising reacting a poly(1,4-butanediol)bis(4-aminobenzoate) of formula [2]

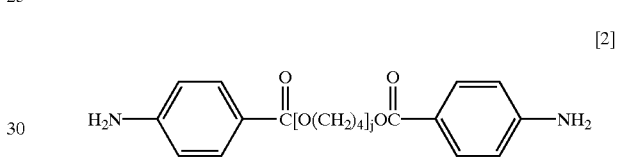

[2]

with an aldehyde represented by formula [3]

$R^2CH=O$  [3]

wherein in formulas [1] and [2], j is an integer of 3 to 30 and in formula [1] and [3], $R^2$ is an unsubstituted homocyclic or heterocyclic aryl radical or alkyl, alkoxy, alkylthio or halogen substituted homocyclic or heterocyclic aryl radical.

9. The method of claim 8 wherein the aldehyde is selected from the group consisting of benzaldehyde, anisaldehyde, furfural, ethoxybenzaldehyde, butoxybenzaldehyde, hexyloxybenzaldehyde, octyloxybenzaldehyde, decyloxybenzaldehyde, dodecyloxybenzaldehyde, hexadecyloxybenzaldehyde, ethylbenzaldehyde, isopropylbenzaldehyde, dimethylbenzaldehyde, and pyridinecarboxaldehyde.

10. A one part composition comprising of:
   (i) a compound or mixture of compounds of formula [1]:

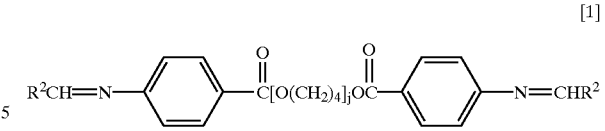

[1]

wherein j is an integer of 3 to 30 and $R^2$ is unsubstituted aryl or heterocyclic aryl radical or alkyl, alleoxy, alkylthio or halogen substituted aryl or heterocyclic aryl radical;
   (ii) an aromatic polyisocyanate and/or a polyurethane/urea prepolymer having terminal aromatic isocyanate groups; and
   (iii) a protic acid or salts thereof.

11. A composition according to claim 10 which is moisture curable and storage stable.

12. A composition according to claim 11 wherein said storage stability in a hermetically sealed package exceeds 6 months at room temperature.

13. A composition according to claim 10 wherein said aromatic polyisocyanate is carbodiimide modified polyisocyanate, biuret modified polyisocyanate, isocyanurate modified polyisocyanate or urethane modified polyisocyanate.

14. A composition according to claim 10 wherein said protic acid is selected from the group consisting of carboxylic, sulfonic, and phosphoric acids.

15. A composition according to claim 14 wherein said carboxylic acids are aromatic carboxylic acids.

16. A composition according to claim 14 wherein said sulfonic acids are aliphatic or aromatic sulfonic acids.

17. The composition of claim 10, further comprising auxiliary agents and/or additives selected from the group consisting of fillers, thixotropic agents, plasticizers, adhesion improvers, metallic powders, inorganic or organic colorants, stabilizers, biocides, and solvents.

18. An adhesive comprising the composition of claim 10 and auxiliary agents and/or additives selected from the group consisting of fillers, thixotropic agents, plasticizers, adhesion improvers, metallic powders, inorganic or organic colorants, stabilizers, biocides, and solvents.

19. An anticorrosive coating comprising the composition of claim 10 and auxiliary agents and/or additives selected from the group consisting of fillers, thixotropic agents, plasticizers, adhesion improvers, metallic powders, inorganic or organic colorants, stabilizers, biocides, and solvents.

20. An anti-fouling paint comprising the composition of claim 10 and auxiliary agents and/or additives selected from the group consisting of fillers, thixotropic agents, plasticizers, adhesion improvers, metallic powders, inorganic or organic colorants, stabilizers, biocides, and solvents.

21. A material for caulking, sealing, wall and roof covering, waterproofing, or flooring, comprising the composition of claim 10 and auxiliary agents and/or additives selected from the group consisting of fillers, thixotropic agents, plasticizers, adhesion improvers, metallic powders, inorganic or organic colorants, stabilizers, biocides, and solvents.

22. A method of protecting a metal or non-metal surface from corrosion, fixation of marine organisms thereto or a combination thereof, comprising contacting said surface to be immersed in seawater with the composition of claim 10, 19, or 20.

23. An article of manufacture comprising a metal or non-metal substrate having the composition of claim 10 applied thereto.

* * * * *